US006551627B1

(12) United States Patent
Yoon et al.

(10) Patent No.: US 6,551,627 B1
(45) Date of Patent: Apr. 22, 2003

(54) MEDICINAL HERBAL COMPOUNDS FOR THE PREVENTION AND TREATMENT OF DIABETES

(75) Inventors: Ji-Won Yoon, Calgary (CA); Hee-Sook Jun, Calgary (CA)

(73) Assignee: Holomed Pharmaceuticals, Ltd., Nassau (BS)

( * ) Notice: Subject to any disclaimer, the term of this patent is extended or adjusted under 35 U.S.C. 154(b) by 0 days.

(21) Appl. No.: 09/847,375

(22) Filed: May 3, 2001

(51) Int. Cl.[7] .................. A61K 35/78; A61K 33/32; A61K 33/24
(52) U.S. Cl. .................. 424/725; 424/728; 424/732; 424/765; 424/639; 424/641; 424/655; 514/866
(58) Field of Search .................. 424/655, 725, 424/728, 732, 765, 639, 641; 514/866

(56) References Cited

U.S. PATENT DOCUMENTS

| | | | | |
|---|---|---|---|---|
| 5,496,553 A | * | 3/1996 | Wilson et al. | |
| 5,773,004 A | * | 6/1998 | Takahashi | |

FOREIGN PATENT DOCUMENTS

| | | | | |
|---|---|---|---|---|
| EP | 0925790 A1 | * | 6/1999 | |
| JP | 62022714 A | * | 1/1987 | |
| JP | 06237735 A | * | 8/1994 | |
| KR | 99073631 A | * | 10/1999 | |
| RO | 106508 B1 | * | 5/1993 | |
| WO | WO 9852587 A | * | 11/1987 | |

OTHER PUBLICATIONS

Shah (Ind. J. Med. Res., 55, 2, 1967).*
Rana et al. (J. Econ. and Tax. Botany, 1999).*
Kim (Saengyak Hakhoechi (1986), 17(1), 35–8).*
Panossian, et al. "Plant adaptogens III. ★Earlier and more recent aspects and concepts on their mode of action", Phytomedicine, vol. 6(4) pp. 287–300 1999.
Ribes, et al. "Effects of Fenugreek Seeds on Endocrine Pancreatic Secretions in Dogs" Ann. Nutr. Metals 28: 37–43 1984.
Srivastava, et al. "Hypoglycemia induced by syzygium cumini linn. Seeds in diabetes mellitus" Asian Med. J. 26(7) pp. 489–491.
Kit S.M., et al., "The study of Hypoglycemic effect of some pre-carpathian plants in experiment" Farmatsevtich. Zhurnal, 1972, No. 4 pp. 61–65.
Hikino et al. "Isolation and Hypoglycemic Activity of eleutherans A, B, C, D, E, F, and G: Glycans of *Eleutheroccus senticosus* roots" Journal of Natural Products vol. 49. No. 2 pp. 293–297,Mar.–Apr. 1986.
Bever et al. "Plants with Oral Hypoglycaemic Action" Quart. J. Crude Drug Res. 17 (1979), No. 3–4 pp. 139–196.
Ghosh et al "Perspectives in Diabetes Genetic Analysis of NIDDM The study of Quantative Traits" Diabetes, vol. 45, Jan. 1996.
Portha et al. "B–Cell Insensitivity to Glucose in the GK Rat, a spontaneous nonobese model for Type II Diabetes" Diabetes, vol. 40, Apr. 1991.

Saad et al " A two–step model for development of non–insulin–dependent diabetes" Feb. 1991 The American Journal of Medicine, vol. 90 pp. 229–235.
Knowler et al. "Gm 3;5,13,14 and Type 2 Diabetes Mellitus: An Association in American Indians with Genetic Admixture" Am. J. Hum. Genet. 43:520–526, 1988.
Helmrich et al. "Physical Activity and Reduced Occurrence of Non–Insulin–Dependent Diabetes Mellitus" New England Journal of Medicine, vol. 325 No. 3, pp 147–152, Jul. 18, 1991.
Lillioja et al. "Insulin Resistance and Insulin Secretory Dysfunction as Precursors of Non–insulin–dependent diabetes mellitus" New England Journal of Medicine, vol. 329 No. 27, pp 1988–1982, Dec. 30, 1993.
Rahilly et al "Type 2 (non–insulin–dependent) diabetes mellitus New genetics for old nightmares" Diabetologia 1988, 31:407–414.
Barnett et al "Diabetes in Identical Twins A Study of 200 pairs" Diabetologia 7, pp 46–49 1971.
J. Kobberling "Studies on the Genetic Heterogeneity of Diabetes Mellitus"Diabetes, vol. 37 pp.667–687 Jun. 1988.
DeFronzo "The Triumvirate: B–Cell, Muscle, Liver A collusion Responsible for NIDDM" Diabetes, vol. 37 pp.667–687 Jun. 1988.
Burant et al. "Diabetes–induced functional and structural changes in insulin receptors from Rat Skeletal Muscle" J Clinical Investigation, Inc. vol. 77, Jan. 1986 pp. 260–270.
Venkatesan et al. "Antidiabetic Action of Vanadyl in Rats Independent of In Vivo Insulin–Receptor Kinase Activity" Diabetes vol. 40, pp. 492–498 Apr. 1991.
Klein et al. "Insulin Activation of Insulin Receptor Tyrosine Kinase in Intact Rat Adipocytes" Journal of Biological Chemistry vol. 261, No. 10, pp. 4691–4697 Apr. 5, 1986.
Giroix et al. "Glucose Insensitivity and Amino–acid Hypersensitivity of Insulin Release in Rats with non–insulin–dependent diabetes—A study of the Perfused Pancreas" Diabetes vol. 32 pp. 445–451 May 1983.
Tan et al. "Concise Review for Primary Care Physicians–Pharmacologic Treatment Options for Non–Insulin– Dependent Diabetes Mellitus" Mayo Clinic Proc., Aug. 1996 vol. 71 pp. 763–768.
Aguilar–Bryan et al. "Cloning of the B Cell High Affinity Sulfonylurea Receptor: A Regultror of Insulin Secretion" Science vol. 268 pp. 423–426 Apr. 21, 1995.
DeFronzo et al. "Pathogenesis of NIDDM—A Balanced Overview" Diabetes Care, vol. 15, No. 3, pp. 318–368 Mar. 1992.

* cited by examiner

*Primary Examiner*—Christopher R. Tate
(74) *Attorney, Agent, or Firm*—Squire, Sanders & Dempsey L.L.P.

(57) ABSTRACT

The invention is directed to a herbal medicinal composition for preventing or treating type II diabetes. The composition is comprised of extracts from *Pterocarpus marsupium, Morus alba, Orthosiphon aristatus, Opiophogon japonicus, Rosa rugosa, Commelina communis, Trichosanthis kirilowii* and *Anemarrhena asphodeloides*.

17 Claims, 6 Drawing Sheets

(2 of 6 Drawing Sheet(s) Filed in Color)

Fig. 5 A ~ H
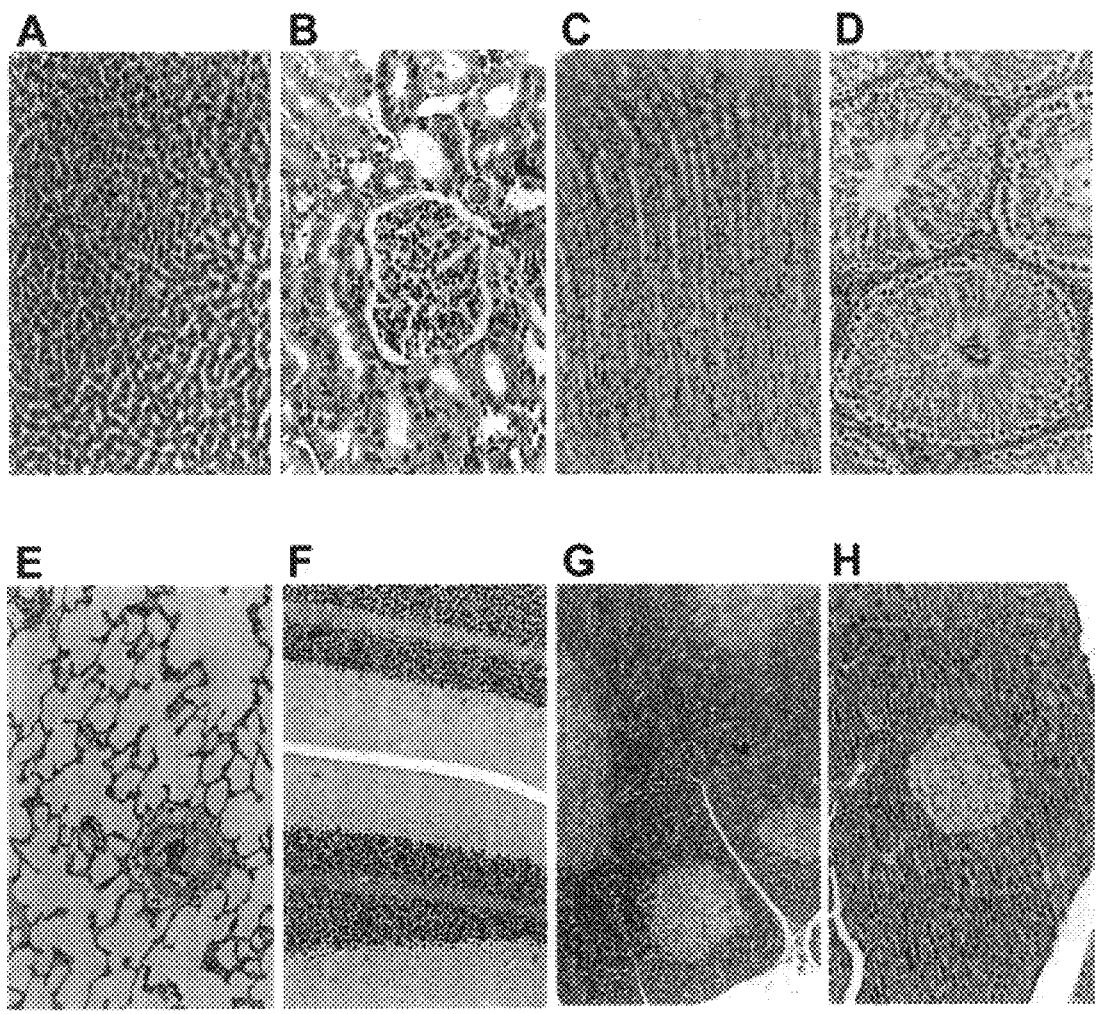

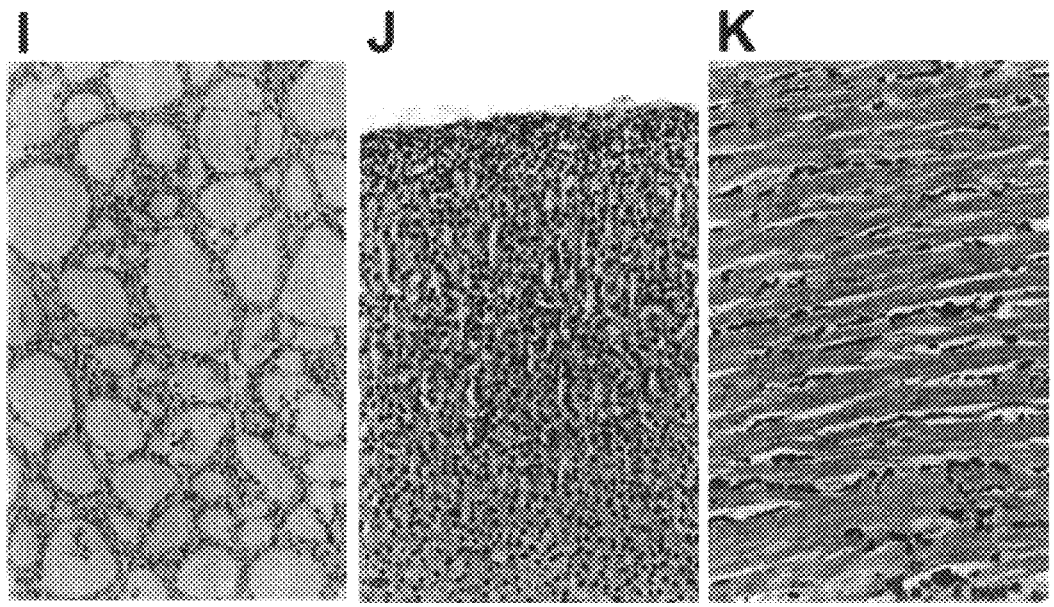
Fig. 5 I - K

MEDICINAL HERBAL COMPOUNDS FOR THE PREVENTION AND TREATMENT OF DIABETES

FIELD OF THE INVENTION

The present invention is related to a medicinal herbal composition for preventing or treating diabetes. The invention also relates to a method of preventing or treating diabetes by administering the composition to an individual.

BACKGROUND OF THE INVENTION

Diabetes mellitus is a common, serious disease characterized by hyperglycemia. The disease can be divided into two major subclasses: insulin-dependent diabetes mellitus (IDDM), also known as type I diabetes, and non-insulin-dependent diabetes mellitus (NIDDM), also known as type II diabetes (World Health Organization Study Group. Diabetes mellitus. WHO Tech. Rep. Ser. 727:1–113, 1985). IDDM results from insulin deficiency caused by cell-mediated autoimmune destruction of pancreatic beta cells, and generally develops in the young (Yoon J W., Insulin-dependent diabetes mellitus. In: Roitt I M and Delves P J. (Eds.) Encyclopedia of Immunology, Second Edition. Academic Press Ltd., London, pp. 1390–1398, 1998; Bach J F., Insulin-dependent diabetes mellitus as a beta cell targeted disease of immunoregulation. J. Autoimm. 8:439–463, 1995). IDDM accounts for approximately 10–15% of the diabetic population worldwide (World Health Organization Study Group. Diabetes mellitus. WHO Tech. Rep. Ser. 727:1–113, 1985). In contrast, NIDDM results from a variable combination of insulin resistance and insulin deficiency, and generally develops in adults (Jun H S, et al., Pathogenesis of non-insulin-dependent (Type II) diabetes mellitus (NIDDM)—Genetic predisposition and metabolic abnormalities. Advanced Drug Delivery Reviews 35:157–177, 1999; DeFronzo R A., The triumvirate:—cell, muscle, liver: a collusion responsible for NIDDM. Diabetes 37:667–687, 1988). However, NIDDM can also develop at a younger age, as seen in the maturity-onset diabetes of the young (Pirart J., Diabetes mellitus and its degenerative complications: a prospective study of 4400 patients observed between 1947 and 1973. Diabetes Care 1:168–188, 1978). NIDDM accounts for over 85% of the diabetic population worldwide. Both IDDM and NIDDM can cause microvascular and macrovascular complications, resulting in increases in morbidity and mortality (Fajans S S, et al., Prediabetes, subclinical diabetes, and latent clinical diabetes: interpretation, diagnosis and treatment. In: Leibel D S, Wrenshall G S. (Eds.) On the Nature and Treatment of Diabetes. Excerpta Medica, Amsterdam, pp. 641–656, 1965).

NIDDM is a complex disease that is currently thought to be influenced by more than a single gene or environmental factor (Ghosh S, et al., Genetic analysis of NIDDM. Diabetes 45:1–14, 1995; Kobberling J. Studies on the genetic heterogeneity of diabetes mellitus. Diabetologia 7:46–49, 1971; Rotter J L, et al., Genetics of diabetes mellitus. In: Rifkin H, Porte D (Eds.) Diabetes Mellitus Theory and Practice. Elsevier, New York, pp. 378–413, 1990). Familial aggregation and the high concordance rate for the disease (60–100%) in identical twins suggest that genetic factors play an important role in the pathogenesis of NIDDM (O'Rahilly S, et al., Type 2 (noninsulin dependent) diabetes mellitus. New genetics for old nightmares. Diabetologia 31:407–414, 1988; Barnett A H, et al., Diabetes in identical twins. A study of 200 pairs. Diabetologia 20:87–93, 1981). In addition, environmental factors such as obesity, physical activity and diet also play a strong role in the development of the disease (Knowler W C, et al., Gm and type 2 diabetes mellitus: an association in American Indians with genetic admixture. Am. J. Hum. Genet. 43:520–526, 1988; Bennett P H, et al., Epidemiology and natural history of NIDDM: non-obese and obese. In: Alberti K G M M, DeFronzo R A, Keen H, Zimmett P (Eds.) International Textbook of Diabetes Mellitus. Wiley, New York, pp. 147–176, 1992; Helmrich S P, et al., Physical activity and reduced occurrence of NIDDM. N. Engl. J. Med 325:147–152, 1991). Although the relative contribution of genetic and environmental factors to the development of NIDDM differs among individuals, patients generally have two common metabolic abnormalities, insulin resistance and defects in glucose-stimulated insulin secretion, which lead to the disease state (Saad M F, et al., A two step model for development of non-insulin-dependent diabetes. Am. J. Med. 90:229–235, 1991; DeFronzo R A, et al., Pathogenesis of NIDDM: A balanced overview. Diabetes Care 15:318–368, 1992; Lillioja S, et al., Insulin resistance and insulin secretory dysfunction as precursors of non-insulin-dependent diabetes mellitus. N. Engl. J. Med. 329:1988–1992, 1993).

The insensitivity of the target tissue in response to insulin (insulin resistance) appears to develop first in genetically predisposed subjects in the presence of the necessary environmental factors (Jun H S, et al., Pathogenesis of non-insulin-dependent (Type II) diabetes mellitus (NIDDM)— Genetic predisposition and metabolic abnormalities. Advanced Drug Delivery Reviews 35:157–177, 1999). To compensate for this, that is, to lower blood glucose and maintain normoglycemia, the secretion of insulin from the beta cells increases, resulting in hyperinsulinemia. Over time, the insulin resistance worsens, and the compensatory action fails, leading eventually to impaired glucose tolerance. Insulin secretion reaches a plateau, and beta cell function is impaired, resulting in insulin deficiency, and leading finally to hyperglycemic NIDDM. In addition, hyperglycemia itself leads to impaired insulin resistance and insulin secretion, exacerbating the disease.

The regulation of diet and exercise and/or treatment with insulin or hypoglycemia drugs have been used for the control of diabetes. Treatment with these agents is successful in some cases, but the mortality index continues to rise. Insulin treatment provides symptomatic relief rather than a cure for NIDDM. Hypoglycemic agents such as sulfonylureas and biguanides (metformin) also lower blood glucose, but again, simply provide symptomatic relief. Sulfonylureas lower the blood glucose level by stimulating the release of insulin from pancreatic beta cells. These agents directly stimulate insulin release by closing adenosyl triphosphate (ATP)-sensitive potassium channels and depolarizing the cell membrane (Aguilar-Bryan L, et al., Cloning of the beta cell high-affinity sulfonylurea receptor: a regulator of insulin secretion. Science 268:423–426, 1995; Tan G H, et al., Pharmacologic treatment options for non-insulin-dependent diabetes mellitus. Mayo Clinic Proceedings 71:763–768, 1996; Lubbos H, et al., Oral hypoglycemic agents in type II diabetes mellitus. American Family Physician. 52:2075–2078, 1995) The side effects of sulfonylureas include hypoglycemia, renal and hepatic disease, gastrointestinal disturbances, increased cardiovascular mortality, dermatological reactions, dizziness, drowsiness and headache. Biguanides lower blood glucose levels by reducing intestinal glucose absorption and hepatic glucose, but not by stimulating insulin secretion. The major side effects of biguanidine are lactic acidosis and increased cardiovascular mortality. Alpha glucosidase inhibitors inhibit intestinal alpha glucosidases and consequently delay the digestion of sucrose and complex carbohydrates. The side effects of alpha glucosidase inhibitors include gastrointestinal side effects and hypoglycemia. Thiazolidinediones improve insulin resistance directly, enhancing the effects of circulating insulin, directly stimulate peripheral glucose uptake and inhibit glucose production in the liver. Thiazolidinediones are only effective in the presence of insulin and may cause red blood cell abnormalities, and headache.

Therefore, more effective drugs for the treatment of diabetes are clearly needed. We have long been interested in medicinal plants as a possible source for the development of hypoglycemic agents, and we have tried to halt the severe long-term complications of NIDDM in patients using extracts from various medicinal plants. We screened many plants and found that certain combinations of plant extracts have hypoglycemic effects. In particular, as exemplified infra, we discovered that the combined extracts, designated medicinal herbal compounds for treatment of type 2 diabetes (MHCTD), from *Pterocarpus marsupium* (Lodha R, et al. Traditional Indian systems of medicine. Ann. Acad. Med. Singapore 29:37–41, 2000; Sheehan E W, et al., A constituent of *Pterocarpus marsupium*, (-)-epicatechin, as a potential antidiabetic agent. J. Nat. Prod. 46:232–234, 1983; Manickam M, et al., Antihyperglycemic activity of phenolics from *Pterocarpus marsupium*. J. Nat. Prod. 60:609–610, 1997), *Morus alba* (Chen F, et al., Hypoglycemic activity and mechanisms of extracts from mulberry leaves (folium mori) and cortex mori radicis in streptozotocin-induced diabetic mice. Yakugaku Zasshi 115:476–482, 1995; Hikino H, et al., Isolation and hypoglycemic activity of moran A, a glycoprotein of *Morus alba* root barks. Planta Med. 2:159–160, 1985; Fukai T, et al., Structures of two natural hypotensive Diels-Alder type adducts, mulberrofurans F and G, from the cultivated mulberry tree (Morus lhou KOIDZ.). Chem Pharm Bull (Tokyo). 33:3195–3204, 1985; Nikaido T, et al., Inhibition of adenosine 3',5'-cyclic monophosphate phosphodiesterase by phenolic constituents of mulberry tree. Chem. Pharm. Bull. (Tokyo). 32:4929–4934, 1984), *Orthosiphon aristatus* (Hsu H Y. Oriental Materia Medica: A Concise Guide. Oriental Healing Art Institute, Long Beach, Calif. p. 297), *Opiophogon japonicus, Rosa rugosa, Commelina communis, Trichosanthis kirilowii* and *Anemarrhena asphodeloides* (Ichik H, et al., New antidiabetic compounds, mangiferin and its glucoside. Biol. Pharm. Bull 21:1389–1390, 1998; Miura T, et al., Antidiabetic effect of seishin-kanro-to in KK-Ay mice. Planta Med. 63:320–322, 1997; Nakashima N, et al., Isolation of pseudoprototimosaponin AIII from rhizomes of Anemarrhena asphodeloides and its hypoglycemic activity in streptozotocin-induced diabetic mice. J. Nat. Prod. 56:345–350, 1993) showed a strong anti-diabetic effect in an animal model, the Goto-Kakizaki (GK) rat. In addition, treatment of NIDDM patients with the combined extracts for 3 months to 1 year significantly reduced blood glucose levels.

SUMMARY OF THE INVENTION

The present invention has met the hereinbefore described need.

An object of the invention is to provide a hypoglycemic effective composition comprising extracts from *Pterocarpus marsupium, Morus alba, Orthosiphon aristatus, Opiophogon japonicus, Anemarrhena asphodeloides*, or *Trichosanthis kirilowii*, in combination with extracts from *Rosa rugosa* and/or *Commelina communis*, and a pharmaceutically acceptable carrier thereof.

The extracts may be present in a relative ratio to each other of:
  about 3% by weight to about 90% by weight of *Pterocarpus marsupium*,
  about 3% by weight to about 90% by weight of *Morus alba*,
  about 3% by weight to about 90% by weight of *Orthosiphon aristatus*,
  about 3% by weight to about 90% by weight of *Opiophogon japonicus*,
  about 3% by weight to about 90% by weight of *Rosa rugosa*,
  about 3% by weight to about 90% by weight of *Commelina communis*,
  about 3% by weight to about 90% by weight of *Trichosanthis kirilowii*, and
  about 3% by weight to about 90% by weight of *Anemarrhena asphodeloides*.

Preferably, the extracts may be present in a ratio of:
  about 5% by weight to about 50% by weight of *Pterocarpus marsupium*,
  about 5% by weight to about 50% by weight of *Morus alba*,
  about 5% by weight to about 50% by weight of *Orthosiphon aristatus*,
  about 5% by weight to about 50% by weight of *Opiophogon japonicus*,
  about 3% by weight to about 50% by weight of *Rosa rugosa*,
  about 3% by weight to about 50% by weight of *Commelina communis*,
  about 3% by weight to about 50% by weight of *Trichosanthis kirilowii*, and
  about 3% by weight to about 50% by weight of *Anemarrhena asphodeloides*.

Still more preferably, the extracts may be present in a ratio of:
  about 20% by weight of *Pterocarpus marsupium*,
  about 15% by weight of *Morus alba*,
  about 20% by weight of *Orthosiphon aristatus*,
  about 10% by weight of *Opiophogon japonicus*,
  about 8% by weight of *Rosa rugosa*,
  about 7% by weight of *Commelina communis*,
  about 10% by weight of *Trichosanthis kirilowii*, and
  about 10% by weight of *Anemarrhena asphodeloides*.

Another object of the invention is to provide the above composition, wherein the carrier is preferably a base of berries or fruit, a base of vegetable soup or bouillon, a soya-milk drink, or a nutritive supplement. In the case of using a base of berries or fruit, the base may be preferably made of extracts from *Rosa canina, Vaccinum myrtillus* and/or *Vaccinum vitis-idea*. In the case where the base is made of vegetable soup or bouillon, the base may be preferably made of extracts from *Urtica diotica* leaves, *Allium cepa*, and/or *Ocimum sanctum*.

The composition above may further include extracts from *Arctium lappa* root, *Eugenia jambolana* seeds, *Phaseus vulgaris* husks, *Trigonella foenum graeam* seeds, and *Vaccinum myrtillus* leaves. Preferably, the extracts may be present in a ratio of:

about 5% by weight to about 20% by weight of *Arctium lappa* root, about 5% by weight to about 70% by weight of *Eugenia jambolana* seeds, about 5% by weight to about 20% by weight of *Phaseus vulgaris* husks, about 10% by weight to about 30% by weight of *Trigonella foenum graeam* seeds, and about 20% by weight to about 60% by weight of *Vaccinum myrtillus* leaves, wherein said ratio is relative to each of the extracts of *Arctium lappa* root, *Eugenia jambolana* seeds, *Phaseus vulgaris* husks, *Trigonella foenum graeam* seeds, and *Vaccinum myrtillus* leaves.

In another embodiment of the invention, the above composition may further comprise chromium, manganese, zinc, niacin, vitamin B6 or vitamin B12. In such a composition, the chromium may be present in an amount of about 20 to about 500 micrograms, manganese may be present in an amount of about 1 to about 10 milligrams, zinc may be present in an amount of about 2 to about 10 milligrams, niacin may be present in an amount of about 50 to about 500 milligrams, vitamin B6 may be present in an amount of about 1 to about 50 milligrams, and vitamin B12 may be present in an amount of about 5 to about 100 micrograms per dose.

Any of the above compositions may further comprise extracts from Acanthopanax, Schizandra, and optionally Rhodiola. Preferably, the extracts of *Acanthopanax senticosus* root, *Schizandra chinensis* fruit and seed, and *Rhodiola rosea* root are present in a ratio of about 4:2:1. An example of a Schizandra fixed combination is disclosed in Herbal Medicinal Product application nos. dnr 96-0045 and dnr 96-0046 before the Swedish Medical Product Agency, "the Swedish FDA". The contents of these applications are incorporated by reference herein in their entirety.

Another object of the invention is to provide a method of treating type II diabetes comprising administering to a person in need thereof an anti-diabetic or hypoglycemic effective amount of any of the above compositions.

In yet another object of the invention, a method of preventing onset of clinical type II diabetes is provided. The method comprises administering to a person in need thereof an anti-diabetic or hypoglycemic effective amount of any of the above compositions.

In still another object of the invention, a method of reducing blood glucose levels in patients who have blood glucose levels of about 200 to about 300 mg/dl at the beginning of treatment, is provided. The method comprises administering to the patient an effective amount of any of the above compositions.

In other embodiments, a method of increasing insulin secretion from pancreatic β cells, comprising administering an effective amount of any of the above compositions to a patient, is provided. A method of inhibiting degradation of complex carbohydrates to monosaccharides, comprising administering any of the above compositions to a patient, is also provided.

In another embodiment of the invention, this application provides for a hypoglycemic effective composition comprising extracts from *Pterocarpus marsupium, Morus alba, Orthosiphon aristatus, Opiophogon japonicus, Anemarrhena asphodeloides*, or a composition comprising extracts from *Arctium lappa* root, *Eugenia jambolana* seeds, *Phaseus vulgaris* husks, *Trigonella foenum graeam* seeds, and *Vaccinum myrtillus* leaves, in combination with extracts from *Rosa rugosa* and/or *Commelina communis*, and a pharmaceutically acceptable carrier thereof.

These and other objects of the invention will be more fully understood from the following description of the invention, the referenced drawings attached hereto and the claims appended hereto.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinbelow, and the accompanying drawings which are given by way of illustration only, and thus are not limitative of the present invention, and wherein;

FIG. 5 shows the non-toxic effect of MHCTD on various organs. Normal WF rats were administered MHCTD at a dose 10 times higher than the regular dose (50 g/kg body weight) daily for 5 months beginning at 3 months of age, and various organs were histologically examined. (A) Liver section showing no sign of lymphocytic infiltration, necrosis or intranuclear glycogen infiltration; (B) kidney section showing intact glomeruli, tubules and vessels with no interstitial lymphocytic infiltration or necrosis. (C) stomach section showing intact mucosa and no sign of inflammatory cell infiltration or other cellular injury; (D) testes section showing no lesions and no cellular changes; (E) lung section showing normal alveoli, bronchioles and bronchi; (F) brain section showing intact nerve and glial cells in the cerebral cortex; (G) thymus section showing no observable lesions; (H) pancreatic section showing an intact morphology of both the endocrine islet and exocrine acinar cells with no evidence of lymphocytic infiltration or necrosis; (I) thyroid section showing no observable lesions; (J) adrenal section showing no observable lesions; and (K) heart section showing normal endocardium and myocardium.

DETAILED DESCRIPTION OF THE INVENTION

Figure 1:
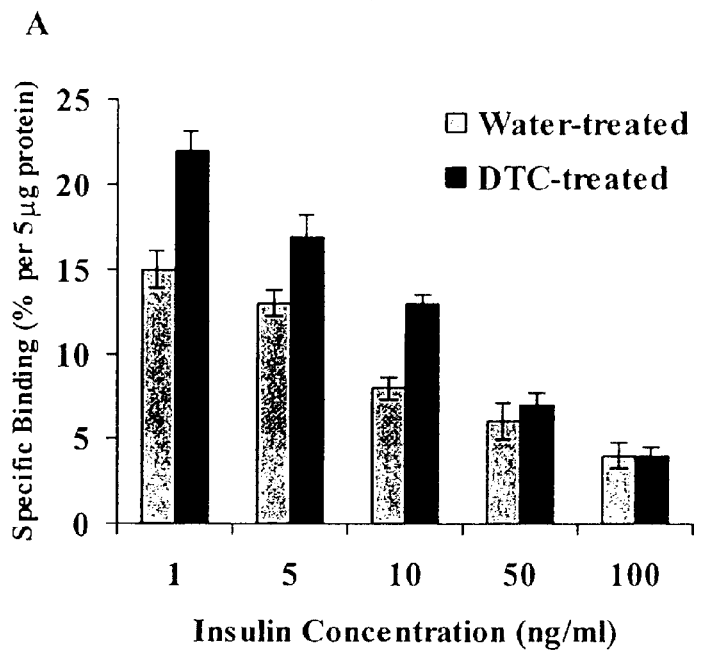
FIG. 1 shows the effect of MHCTD on insulin binding to its hepatocyte and muscle receptors. The insulin receptors were partially purified from hepatocytes (A) or hindlimb skeletal muscle (B) of GK rats that were treated with MHCTD or water for 5 months, and the rate of insulin binding to these receptors was determined.
Figure 1:
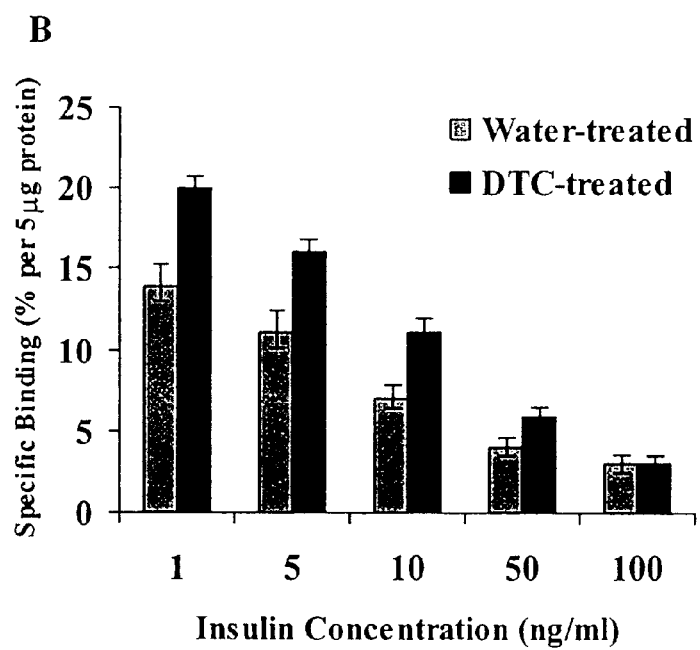

The present invention is directed to a herbal medicinal composition that can be administered to a personal suffering from diabetes, preferably type II diabetes, which results in the lowering of the blood glucose level of the patient. Administration of the composition to the patient both prevented and treated incidences of clinical diabetes.

As used herein, "anti-diabetic" or "hypoglycemic" compound or composition generally refers to an agent that lowers blood glucose levels. As a general guideline, without being limited to the values suggested herein, if blood glucose level is decreased by at least about 100 mg/dl, then the compound is considered to be a hypoglycemic agent. For example, if the patient has a blood glucose level of 380 mg/dl before treatment, which decreases to 280 mg/dl after treatment, then the treatment is considered to be a hypoglycemic agent. Such an agent or any other agent that may lower blood glucose levels to other accepted standards of hypoglycemic effect, may be used to treat diabetes or to prevent the incidence of diabetes. The hypoglycemic or anti-diabetic effect can be measured by a variety of methods including, but not limited to, measuring the blood glucose levels, the rate of insulin binding to its receptor, the level of insulin secretion from pancreatic beta cells, and inhibition of glucohydrolase activity.

As used herein, "extract" refers to a concentrated preparation of the essential constituents of the medicinal plant. Typically, an extract is prepared by drying and powderizing the plant. Optionally, the plant, the dried plant or the powderized plant may be boiled in solution. The extract may be used in liquid form, or it may be mixed with other liquid or solid medicinal herbal extracts. Alternatively, the medicinal herbal extract may be obtained by further precipitating solid extracts from the liquid form.

In further detail and/or alternatively, "extract" refers to a concentrated preparation of the essential constituents of the medicinal plant. Typically, an extract is prepared by drying and subsequently cutting or grinding the dried material. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by carbon-dioxide hypercritical (temperature/pressure) extraction. The extract may then be further evaporated and thus concentrated to yield a soft extract (extractum spissum) and/or eventually a dried extract, extracum siccum, by means of spray drying, vacuum oven drying, fluid-bed drying or freeze-drying.

The herbal composition is made by drying and grinding various herbs chosen from *Pterocarpus marsupium, Morus alba, Orthosiphon aristatus, Opiophogon japonicus, Anemarrhena asphodeloides, Trichosanthis kirilowii, Rosa rugosa,* and *Commelina communes*. Most preferably, all of the herbs are used together in various ratios. But it is understood that not all of these herbs may be necessary for the desired effect of reducing blood glucose levels in a patient. Any combination of these herbs may be used so long as the composition lowers blood glucose levels in the patient when administered to the patient.

In an embodiment of the invention, the herbal composition of the invention may comprise any anti-diabetic, hypotensive plant extract that is used in combination with *Rosa rugosa,* and/or *Commelina communis*. Preferably, the above-cited *Pterocarpus marsupium, Morus alba, Orthosiphon aristatus, Opiophogon japonicus, Anemarrhena asphodeloides, Trichosanthis kirilowii* plant extracts may be used in combination with *Rosa rugosa,* and/or *Commelina communis* to form an anti-diabetic composition. Preferably, such a composition comprising Rosa rugosa, and/or *Commelina communis* will have a synergistic anti-diabetic activity. Even more preferably, the anti-diabetic composition may comprise all of the plant extracts of *Pterocarpus marsupium, Morus alba, Orthosiphon aristatus, Opiophogon japonicus, Anemarrhena asphodeloides, Trichosanthis kirilowii, Rosa rugosa,* and *Commelina communis*. Moreover, in this composition, *Trichosanthis kirilowii* may be substituted with a composition comprising extracts from *Arctium lappa* root, *Eugenia jambolana* seeds, *Phaseus vulgaris* husks, *Trigonella foenum graeam* seeds, and *Vaccinum myrtillus* leaves.

The ratio of the extracts in the herbal composition may be the following relative to each other:

- about 3% to about 90%, preferably about 5% to about 50%, even more preferably about 6% to about 30%, and most preferably about 20% by weight of *Pterocarpus marsupium,*
- about 3% to about 90%, preferably about 5% to about 50%, even more preferably about 6% to about 30%, and most preferably about 15% by weight of *Morus alba,*
- about 3% to about 90%, preferably about 5% to about 50%, even more preferably about 6% to about 30%, and most preferably about 20% by weight of *Orthosiphon aristatus,*
- about 3% to about 90%, preferably about 5% to about 50%, even more preferably about 6% to about 30%, and most preferably about 10% by weight of *Opiophogon japonicus,*
- about 3% to about 90%, preferably about 3% to about 50%, even more preferably about 6% to about 20%, and most preferably about 8% by weight of *Rosa rugosa,*
- about 3% to about 90%, preferably about 3% to about 50%, even more preferably about 5% to about 20%, and most preferably about 7% by weight of *Commelina communis,*
- about 3% to about 90%, preferably about 3% to about 50%, even more preferably about 5% to about 20%, and most preferably about 10% by weight of *Trichosanthis kirilowii,* and
- about 3% to about 90%, preferably about 3% to about 50%, even more preferably about 5% to about 20%, and most preferably about 10% by weight of *Anemarrhena asphodeloides.*

In a preferred embodiment, a composition comprising extracts from *Arctium lappa* root, *Eugenia jambolana* seeds, *Phaseus vulgaris* husks, *Trigonella foenum graeam* seeds, and *Vaccinum myrtillus* leaves, may substitute for *Trichosanthis kirilowii* in any anti-diabetic herbal combination in which an extract of *Trichosanthis kirilowii* is used.

Thus, according to one aspect, the invention relates to pharmaceutical compositions containing an anti-diabetic, hypoglycemic effective amount of the herbal compounds of the invention, mixed with suitable pharmaceutically acceptable excipients.

In an alternate embodiment of the invention, the herbal composition may comprise extracts from the following plants: *Arctium lappa* root (Burdock), *Eugenia jambolana* seeds (Java plum, syn. *Syzygium cuminii*), *Phaseus vulgaris* husks (Bean husks), *Trigonella foenum graeam* seeds (Fenugreek seeds), and *Vaccinum myrtillus* leaves (Bilberry leaves). These plant extracts may be used individually or in combination, so long as anti-diabetic effect is maintained. A ratio of these plant extracts may be the following relative to each other:

about 5% to about 20%, preferably about 7% to about 15%, more preferably about 10% by weight of *Arctium lappa* root, about 5% to about 70%, preferably about 7% to about 25%, more preferably about 20% by weight of *Eugenia jambolana* seeds, about 5% to about 20%, preferably about 7% to about 15%, more preferably about 10% by weight of *Phaseus vulgaris* husks, about 10% to about 30%, preferably about 15% to about 25%, more preferably about 20% by weight of *Trigonella foenum graeam* seeds, and about 20% to about 60%, preferably about 30% to about 50%, more preferably about 40% by weight of *Vaccinum myrtillus* leaves.

In still another alternate embodiment of the invention, the medicinal herbal composition may comprise extracts of *Acanthopanax senticosus* root, *Schizandra chinensis* fruit and seed, and/or *Rhodiola rosea* root. These plant extracts may be used individually or in combination, so long as anti-diabetic effect is maintained. A ratio of these plant extracts may be about 4:2:1, respectively, relative to each other. Furthermore, at least Eleutherococcus B and E, Schizandrine, a-schizandrine, salidroside, and/or rosavine are active ingredients of these plant extracts.

In still another alternate embodiment, an active composition may be made from a mixture of chromium, manganese, zinc, niacin, vitamin B6 and vitamin B12. Preferably, the chromium is present in an amount of about 20 to about 500 micrograms, manganese is present in an amount of about 1 to about 10 milligrams, zinc is present in an amount of about 2 to about 10 milligrams, niacin is present in an amount of about 50 to about 500 milligrams, vitamin B6 is present in an amount of about 1 to about 50 milligrams, and vitamin B12 is present in an amount of about 5 to about 100 micrograms per dose.

As used herein, a "dose" refers to a specified quantity of a therapeutic agent prescribed to be taken at one time or at stated intervals.

It will be readily apparent that all of the above compositions in their alternate forms may be used alone or in combination to provide an anti-diabetic herbal medicine, which when administered to a patient, results in diabetes preventive or therapeutic effect.

Depending on the specific clinical status of the disease, administration can be made via any accepted systemic delivery system, for example, via oral route or parenteral route such as intravenous, intramuscular, subcutaneous or percutaneous route, or vaginal, ocular or nasal route, in solid, semi-solid or liquid dosage forms, such as for example, tablets, suppositories, pills, capsules, powders, solutions, suspensions, cream, gel, implant, patch, pessary, aerosols, collyrium, emulsions or the like, preferably in unit dosage forms suitable for easy administration of fixed dosages. The pharmaceutical compositions will include a conventional carrier or vehicle and, in addition, may include other medicinal agents, pharmaceutical agents, carriers, adjuvants, and so on. In the invention, the carrier for the herbal composition may preferably include, a base of berries or fruit, a base of vegetable soup or bouillon, a soya-milk drink, or a nutritive supplement.

If a vegetable soup or bouillon base is desired to be used as a base for the herbal composition, it can be readily seen that any vegetable soup or bouillon base can be used, so long as the anti-diabetic effect of the herbal composition is maintained. Preferably, the vegetable soup or bouillon may be made from extracts of *Urtica diotica* leaves, *Allium cepa*, and/or *Ocimum sanctum*. However, it is understood that any of these components alone or in combination may be used as base for the inventive composition.

If it is desired that the base be made from extracts of berries or fruits, then it is understood that any berry or fruit base may be used so long as its use does not interfere with the anti-diabetic effectiveness of the herbal medicinal composition. Preferably, such berries and fruits may comprise extracts from *Rosa canina* (dog rose), *Vaccinum myrtillus* (bilberry), and/or *Vaccinum vitis-idea* (ligonberry). However, it is understood that any of these components alone or in combination may be used as base for the inventive composition.

If the inventive composition is desired to be placed into a soya milk, it is understood that such a drink will need to be refrigerated to prevent toxic effects. It is further understood that the inventive composition may be placed, mixed, added to or combined with any other nutritional supplement so long as the anti-diabetic effect of the herbal composition is maintained.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, and so on.

The amount of the herbal medicine in a formulation can vary within the full range employed by those skilled in the art, e.g., from about 0.01 weight percent (wt %) to about 99.99 wt % of the medicine based on the total formulation and about 0.01 wt % to 99.99 wt % excipient.

The preferred mode of administration, for the conditions mentioned above, is oral administration using a convenient daily dosage regimen which can be adjusted according to the degree of the complaint. For said oral administration, a pharmaceutically acceptable, non-toxic composition is formed by the incorporation of the herbal composition in any of the currently used excipients, such as, for example, pharmaceutical grades of mannitol, lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt % and 99.99 wt % of the active compound according to this invention.

In one embodiment, the compositions will have the form of a sugar coated pill or tablet and thus they will contain, along with the active ingredient, a diluent such as lactose, sucrose, dicalcium phosphate, and the like; a disintegrant such as starch or derivatives thereof; a lubricant such as magnesium stearate and the like; and a binder such as starch, polyvinylpyrrolidone, acacia gum, gelatin, cellulose and derivatives thereof, and the like.

It is understood that by "pharmaceutical composition" or "herbal medicinal composition", it is meant that the herbal composition is formulated into a substance that is to be administered purposefully for treating or preventing diabetes, preferably type II diabetes, in an individual. The mode of action is believed to be by the reduction of blood glucose levels. However, it is understood that the herbal composition per se will not have a toxic effect.

The invention is also directed to a method of treating type II diabetes comprising administering to a person in need thereof an effective amount of the composition described above.

Furthermore, in another embodiment of the invention, a method of preventing onset of clinical type II diabetes is disclosed, which method comprises administering to a person in need thereof an anti-diabetic, hypoglycemic effective amount of the composition described above.

In still another embodiment of the invention, a method of reducing blood glucose levels in patients who have blood glucose level of about 200 to about 300 mg/dl at the beginning of treatment is described, which method comprises administering to a patient an anti-diabetic, hypoglycemic effective amount of the composition described above.

In another embodiment, the application discloses a method of increasing insulin secretion from pancreatic β cells in a patient, comprising administering an effective amount of the herbal medicine composition described above to the patient.

In still another embodiment, the invention is directed to a method of inhibiting degradation of complex carbohydrates to monosaccharides, comprising administering an effective amount of the above described herbal composition to a patient.

The invention is described in further detail herein below.

NIDDM is a mild form of diabetes that often develops gradually during middle age. However, later stages of this disease are very severe, resulting in long-term complications such as disease of the kidneys, heart, eyes, nerves and other organs. Unlike IDDM, diabetes does not develop from destruction of the pancreatic beta cells, but rather NIDDM develops by mechanisms such as insulin resistance, down-regulation of insulin receptors, defects in insulin secretion from the pancreatic beta cells and other changes to the glucose transporter system. Although many hypoglycemic agents including insulin, sulfonyl-urea and metformin have been used for the treatment of NIDDM, various side effects have been observed, and these agents give symptomatic relief rather than acting as a permanent treatment for NIDDM. Therefore, this investigation was initiated to develop anti-diabetic agents without significant side effects for the treatment of NIDDM using medicinal plant extracts.

We screened several medicinal plants and combinations of medicinal plants which are considered to improve the control of blood glucose, and found that MHCTD showed a strong blood glucose lowering effect in GK rats, an NIDDM animal model.

We also treated 65 randomly selected NIDDM human patients that had different initial ranges of blood glucose levels (200–600 mg/dl) with MHCTD for 3 to 6 months and found that MHCTD clearly lowered blood glucose levels and prevented the long-term complications of diabetes. MHCTD treatment was generally more effective in patients who had a lower blood glucose level in the beginning of treatment (200–300 mg/dl) compared to those who had a higher blood glucose level (400–600 mg/dl). In addition, the lowered blood glucose levels remained after 2 months after termination of the MHCTD treatment. These results indicate that MHCTD has an anti-diabetic effect in NIDDM patients.

Decreased insulin-stimulated glucose uptake is a characteristic of insulin resistance in NIDDM. The reduced number of insulin receptors and/or reduced tyrosine kinase activity of the insulin receptor may be the mechanisms involved in this insulin resistance. Thus, we examined the rate of insulin binding to its receptor in MHCTD-treated GK rats to determine whether the enhancement of insulin receptor binding might be the mechanism for the blood glucose level lowering effect on animal and human NIDDM. We found that the rate of insulin binding to insulin receptors from both hepatocytes and smooth muscle was significantly increased in MHCTD-treated GK rats as compared with water-treated GK rats, indicating that MHCTD treatment can upregulate insulin receptors.

Glucose levels are maintained in normal subjects by a balance between insulin secretion from pancreatic beta cells and insulin action in the splanchnic (liver and gut) and peripheral (muscle and adipose) tissues. If this balance is broken by impaired beta cell function and/or abnormal insulin action, then NIDDM develops. Therefore, the decrease of insulin secretion from the pancreatic beta cells is one of the mechanisms involved in the development of NIDDM. To determine whether MHCTD has any advantageous effect on insulin secretion in pancreatic beta cells, we examined the effect MHCTD on insulin secretion in GK rats. We found that MHCTD treatment increased insulin secretion from the pancreatic beta cells of GK rats. This result suggests that MHCTD contains a component that can enhance insulin secretion, resulting in a lower blood glucose level.

Complex carbohydrates in the diet are degraded into monosaccharides and absorbed in the gastrointestinal tract. Since less biologically active insulin is produced in NIDDM patients, glucose is not utilized properly. Therefore, if the production of glucose from complex carbohydrates is inhibited, then a lower amount of insulin will be required to utilize glucose. Alpha-glucohydrolase catalyzes the enzymatic degradation of complex carbohydrates into monosaccharides (glucose). It is possible that MHCTD may inhibit alpha-glucohydrolase activity and decrease the blood glucose level. We measured blood glucose levels in normal MHCTD-treated WF rats after a starch feeding and found that the blood glucose level was lower than that of water-treated, starch-fed WF rats. This may be due to the inhibition of the degradation of complex carbohydrates to monosaccharides, suggesting that alpha-glucohydrolase may be inhibited in MHCTD-treated WF rats, since both insulin secretion and insulin action are normal in WF rats.

In hyperglycemic animal models, the expression of Glut2 in the pancreatic beta cells was markedly decreased. It has been proposed that a loss of glucose-induced insulin secretion in NIDDM patients is caused by impaired glucose entry into beta cells. Therefore, we determined whether the level of Glut2 protein in pancreatic beta cells was changed in MHCTD-treated GK rats. We found that the expression of Glut2 protein was increased approximately two-fold compared with water-treated control GK rats. This result suggests that MHCTD treatment may also increase the expression of Glut2 to improve glucose uptake, subsequently increasing the secretion of insulin and lowering blood glucose.

Type 2 diabetes is a complex disease that is influenced by genetic and environmental factors. The symptoms at the onset of the disease can be mild, but the severity of the disease gradually increases. Long-term diabetics show increased risk for complications such as neuropathy, retinopathy, renopathy and infections. Therefore, appropriate treatment in the early stages may result in the prevention of these long-term complications. So far, many hypoglycemic agents have been used for the control of blood glucose levels. However, many of these agents have significant side effects. Therefore, efficient anti-diabetic agents without side effects are absolutely necessary for the control of diabetes as well as for the prevention of long-term complications. Our newly developed medicinal herbal compound appears to be an ideal anti-diabetic agent, since many of the diabetic patients who have received this compound report good control of blood glucose without any appearance of side effects and the prevention of long-term complications. In addition, the treatment of a good number of patients who had long-term complications with this medicinal herbal mixture (MHCTD) resulted in a great improvement or remission of the long-term complications.

The following examples are offered by way of illustration of the present invention, and not by way of limitation.

EXAMPLES

Example 1

Materials And Methods—Extraction of Medicinal Plants

*Pterocarpus marsupium* was cultivated in India; the inside of the trunk was harvested and dried. *Morus alba* was cultivated in Korea and northern China; the leaves and roots were harvested and dried. *Orthosiphon aristatus* was cultivated in Vietnam; the whole plant, including roots, branches and leaves, was harvested and dried. *Opiophogon japonicus*, *Rosa rugose* var *typica* (Regel) and *Trichosanthis kirilowii* (Maxim) and *Anemarrhena asphodeloides* (Bunge) were cultivated in Korea and northern China; the roots were harvested and dried. *Commelina communis* (L.) was cultivated in Korea and China; the leaves, stems and flowers were harvested and dried. Each dried component was powdered and mixed (*P. marsupium* (about 20%), *O. aristatus* (about 20%), *M. alba* (about 15%), *O. japonicus* (about 10%), *T. kirilowii* (about 10%), *A. asphodeloides* (about 10%), *R. rugosa* (about 8%) and *C. communis* (about 7%) w/w. Forty grams of the combined plant powder in 200 ml of water was boiled in a slow cooker until the volume was reduced to 100 ml. This mixture was designated medicinal herbal compounds for treatment of type 2 diabetes (MHCTD).

Example 2

Goto-Kakizaki (GK) Rats

The GK rat (Goto Y, et al., Spontaneous diabetes produced by selective breeding of normal Wistar rats. Proc. Japan. Acad. 51:80–85, 1975; Sugiyama Y, et al., Role of hepatic insulin sensitivity in development of hyperglycemia of spontaneously diabetic GK rats. J. Japan. Diab. Soc. 32:593–599, 1989) is one of the best animals for the study of NIDDM, as most of these animals develop diabetes at about 3 months of age and the diabetic syndrome shares many pathological features with human NIDDM. GK rats show impaired insulin secretion and peripheral insulin resistance. Insulin response, sensitivity of glycogen synthesis, lipogenesis and DNA synthesis in the hepatocytes of GK rats are markedly reduced as compared with non-diabetic control rats. In GK rats, the islet structure is disrupted and areas of pronounced fibrosis are seen in the stroma. As the disease progresses, beta cell degranulation is observed, while lymphocytic infiltration of the islets is not. Diabetic complications such as neuropathy and nephropathy are found in these rats. We obtained GK rats from Japan and used these animals to test the effect of MHCTD on hyperglycemia.

Example 3

Administration of MHCTD to GK Rats

To study the effect of MHCTD on the control of blood glucose in diabetic GK rats, 3 month-old rats were treated for 5 months with MHCTD prepared as described above. The animals were intubated daily (10:00 am) with 2.5 ml (5 g/kg body weight). Age- and sex-matched GK rats were intubated with an equal volume of water as a control. Blood glucose levels were measured weekly using a One Touch glucometer until 1 year of age.

To study the effects of MHCTD on the prevention of diabetes, MHCTD treatment of GK rats began at 3 weeks of age, prior to the onset of NIDDM. Rats were intubated daily with MHCTD (5 g/kg body weight) or water as described above until 13 weeks of age, and blood glucose levels were measured weekly until 13 weeks of age.

Example 4

Analysis of the Expression of Insulin Receptors

Insulin receptors were purified from the hepatocytes and skeletal muscle of GK rats treated with MHCTD for 5 months beginning at 3 months of age using wheat germ agglutinin agarose (Klein H H, et al., Insulin activation of insulin receptor tyrosine kinase in intact rat adipocytes. An in vitro system to measure histone kinase activity of insulin receptors activated in vivo. J. Biol. Chem. 261:4691–4697, 1986; Burant C F, et al., Diabetes-induced functional and structural changes in insulin receptors from rat skeletal muscle. J. Clin. Invest. 77:260–270, 1986; Venkatesan N, et. at., Antidiabetic action of vanadyl in rats independent of in vivo insulin-receptor kinase activity. Diabetes 40:492–498, 1991). The rate of insulin binding to solubilized receptors was determined using [$^{125}$I]-labeled insulin. Briefly, the hepatocytes or muscle tissue were homogenized in 4 volumes of 25 mM Hepes (pH 7.4), 5 mM EDTA, 1 TIU/ml aprotinin, 2 mM phenylmethylsulfonyl fluoride (PMSF) and 1% Triton X-100. The homogenate was centrifuged at 10,000 g for 10 min, and the supernatant was stirred at room temperature for 1 hr. The mixture was then centrifuged at 150,000 g for 90 min. The receptors were further purified by adsorption to and elution from agarose-bound WGA. Receptors were eluted from the WGA column with 25 mM Hepes (pH 7.4), 0.1% Triton X-100 containing 0.3 M N-acetylglucosamine. The WGA eluate (50 microliters) was incubated with 10,000 cpm [$^{125}$I]-labeled insulin (specific activity: 125–175 microCi/micrograms) and with increasing concentrations of unlabeled insulin for 16 hr at 4° C. in a buffer containing 25 mM Hepes, 0.1% Triton X-100, 150 mM NaCl, 0.1% bovine serum albumin and 100 U/ml Bacitracin. The receptor and bound insulin were precipitated by the addition of 100 microliters of 0.3% bovine gamma-globulin and 300 microliters of 25% polyethylene glycol and collected by centrifugation. The resulting pellet was washed with 12% polyethylene glycol and counted in a Beckman Instruments gamma counter. The binding was related to the protein concentration in the WGA eluate. As a control, insulin receptors were purified from the GK rats treated with water.

Example 5

Analysis of Insulin Secretion in Pancreatic Beta Cells

GK rats treated with MHCTD or with water for 5 months beginning at 3 months of age were anaesthetized with phenobarbital. The pancreas was perfused as described previously (Portha B, et al., Beta-cell insensitivity to glucose in the GK rat, a spontaneous nonobese model for type II diabetes. Diabetes 40:486–491, 1991; Giroix M H, et a., Glucose insensitivity and amino-acid hypersensitivity of insulin release in rats with non-insulin-dependent diabetes. A study with the perfused pancreas. Diabetes 32:445–451, 1983) using Krebs-Ringer bicarbonate buffer (118 mM NaCl, 4 mM KCl, 2.5 mM $CaCl_2$, 1.2 mM $MgSO_4$, 1.2 mM $KH_2PO_4$, 25 mM $NaHCO_3$, 1.2 g/L bovine serum albumin and 40 g/L dextran) containing 16 mM glucose. The effluent was collected from the cannula in the portal vein at 2 min intervals and stored at −20° C. Insulin secretion was measured and calculated as described previously (Venkatesan N, et al., Antidiabetic action of vanadyl in rats independent of in vivo insulin-receptor kinase activity. Diabetes 40:492–498, 1991; Portha B, et al., Beta-cell insensitivity to glucose in the GK rat, a spontaneous nonobese model for type II diabetes. Diabetes 40:486–491, 1991). Briefly, plasma immunoreactive insulin was estimated using purified rat insulin as a standard. The insulin secretion rate per total pancreas was calculated using the flow rate and expressed as nM/min.

Example 6

Analysis of Alpha-glucohydrolase Reaction

We tested whether the degradation of complex carbohydrates into monosaccharides by alpha-glucohydrolase-catalyzed enzymatic reactions is inhibited by treatment with the combined plant extracts. Wistar Furth (WF) rats treated with MHCTD (5 g/kg body weight) or water for 2 weeks were fasted overnight and intubated with heat-hydrolyzed starch (2 g/kg) suspended in water (2 g/20 ml). Blood samples were collected at 50 min after intubation, and blood glucose levels were determined.

Example 7

Analysis of the Expression of Glucose Transporters

The expression level of glucose transporter 2 (Glut2) in the pancreatic beta cells was determined by Western blot. GK rats treated with MHCTD or water beginning at 3 months of age were sacrificed at 5 months after treatment. Pancreatic islet cell and muscle tissue extracts were prepared and western blot was performed using anti-Glut2 and anti-Glut4 antibodies (Santa Cruz Biotech. Inc., Santa Cruz, Calif.). The reactive bands were visualized using an enhanced chemoluminescence system (Amersham, Oakville, Ontario). The signal was analyzed by densitometric analysis and normalized by the signal of anti-glyceraldehyde-3-phosphate dehydrogenase (GAPDH) antibody-reactive bands.

Example 8

Examination of Toxicity

Normal WF rats (n=40) were intubated with MHCTD (50 g/kg body weight with extract that was concentrated 10×) daily for 5 months beginning at 3 months of age. Each animal was sacrificed by $CO_2$ inhalation. The stomach, testes, adrenal glands, thyroid gland, thymus, lung, heart, kidney, liver, brain and pancreas were removed, fixed with formalin and embedded in paraffin. The paraffin-embedded blocks were sectioned and stained with hematoxylin and eosin as described previously (Baek H S, et al., Direct involvement of macrophages in destruction of beta-cells leading to development of diabetes in virus-infected mice. Diabetes 40:1586–1597, 1991; Yoon J W, et al., Control of autoinmmune diabetes in NOD mice by GAD expression or suppression in beta cells. Science 284:1183–1187, 1999).

Example 9

Treatment of NIDDM Patients with Combined Plant Extracts, MHCTD

To examine the effect of the combined plant extracts on NIDDM patients, 40 g of the extracts combined in the proportions described in Example 1 was mixed with 800 ml of water and slowly boiled for 6 to 12 hr until the volume was reduced by one-half. The supernatant was filtered to remove the precipitate and the filtered extract was divided into 4 portions; each aliquot contained 100 ml of the combined plant extracts. The extract was administered orally to NIDDM patients 1 hour before breakfast, between meals and before sleep for 3 months to 1 year. Blood glucose levels were measured before treatment began, after 3 months of treatment and 2 months after termination of treatment.

Example 10

Results—Effect of Combined Plant Extracts (MHCTD) on Blood Glucose Level in GK Rats To examine the effect of the combined plant extracts on the control of blood glucose levels in GK rats, an animal model of NIDDM, GK rats were treated with extract prepared as described in the Example 1. We found that GK rats treated daily with MHCTD for 5 months, commencing at 3 months of age, showed a significantly decreased incidence of diabetes as compared with water-treated control GK rats. After 3 months, the MHCTD-treated GK rats showed a decrease in disease incidence to 40% with a mean blood glucose level of 223 mg/dl. After 5 months of MHCTD treatment, GK rats showed a decrease in disease incidence to 13%, while the water-treated control GK rats had a disease incidence of 93% (Table 1). When we monitored blood glucose levels for a further 4 months after termination of MHCTD treatment, we found that the blood glucose levels were within the normal range, although slightly increased (Table 2).

Example 11

Effect of MHCTD on the Prevention of Diabetes in GK Rats

To see whether the treatment of GK rats with MHCTD at an early age could prevent the onset of clinical diabetes, we treated 3 week-old pre-diabetic GK rats with MHCTD and examined blood glucose levels. We found that only 10% of the MHCTD-treated rats became diabetic by 9 or 13 weeks of age, whereas 65% of the water-treated control rats were hyperglycemic at 9 weeks and 85% of the animals had become diabetic by 11–13 weeks of age (Table 3).

Example 12

Effect of MHCTD on the Expression of Insulin Receptors

To determine the effect of MHCTD on the expression of insulin receptors, we measured the rate at which insulin binds to the receptors in MHCTD-treated GK rats. The rate of insulin binding to purified insulin receptors from hepatocytes and muscle cells was significantly increased in MHCTD-treated GK rats compared with water-treated controls (FIGS. 1A, 1B). These results indicate that MHCTD may enhance the expression of insulin receptors.

Example 13

Effect of MHCTD on Insulin Secretion in Pancreatic Beta Cells

Figure 2:
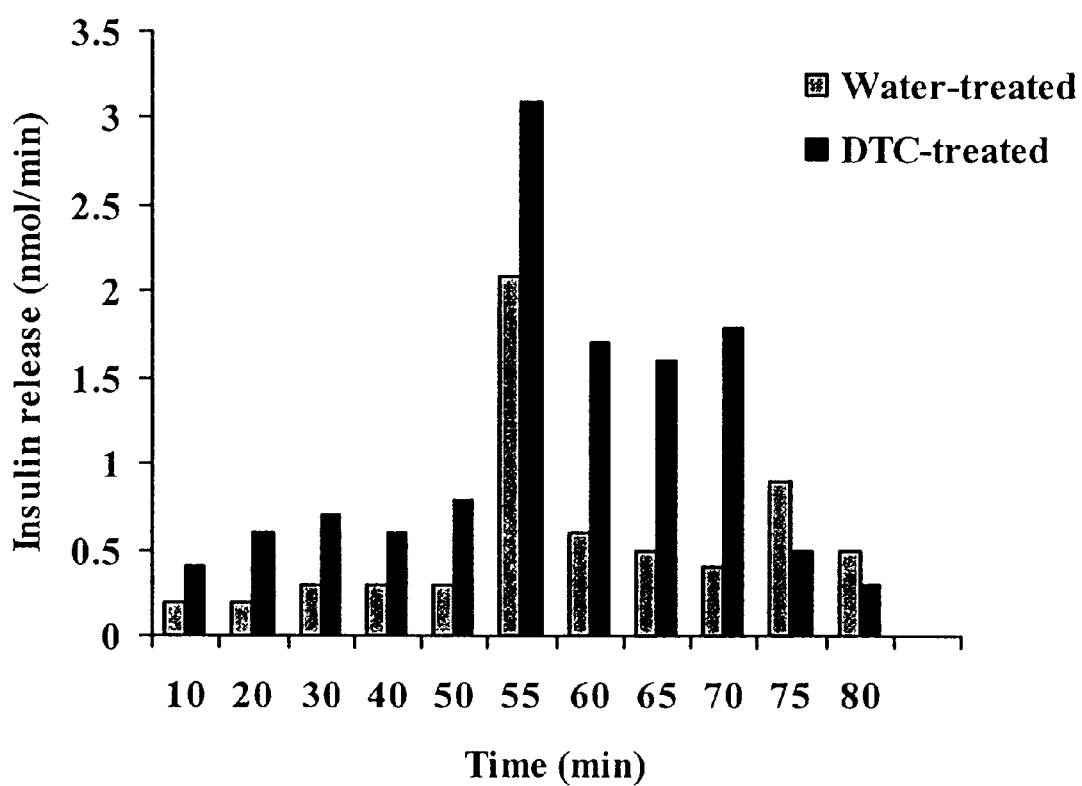
FIG. 2 shows the effect of MHCTD on insulin secretion from pancreatic beta cells. GK rats that were treated with MHCTD or water for 5 months were anesthetized with phenobarbital. The pancreas was perfused with buffer containing 16 mM glucose, the effluent was collected at 2 min intervals and the insulin secretion was measured.

To see whether MHCTD has any effect on insulin secretion from pancreatic beta cells, the insulin level in the blood was measured. We found that the secretion of insulin from MHCTD-treated GK rats was clearly increased compared to water-treated control GK rats (FIG. 2). This result suggests that MHCTD may enhance the secretion of insulin from pancreatic beta cells, probably as a result of an increase in insulin synthesis.

Example 14

Effect of MHCTD on the Inhibition of Alpha-glucohydrolase

Figure 3:
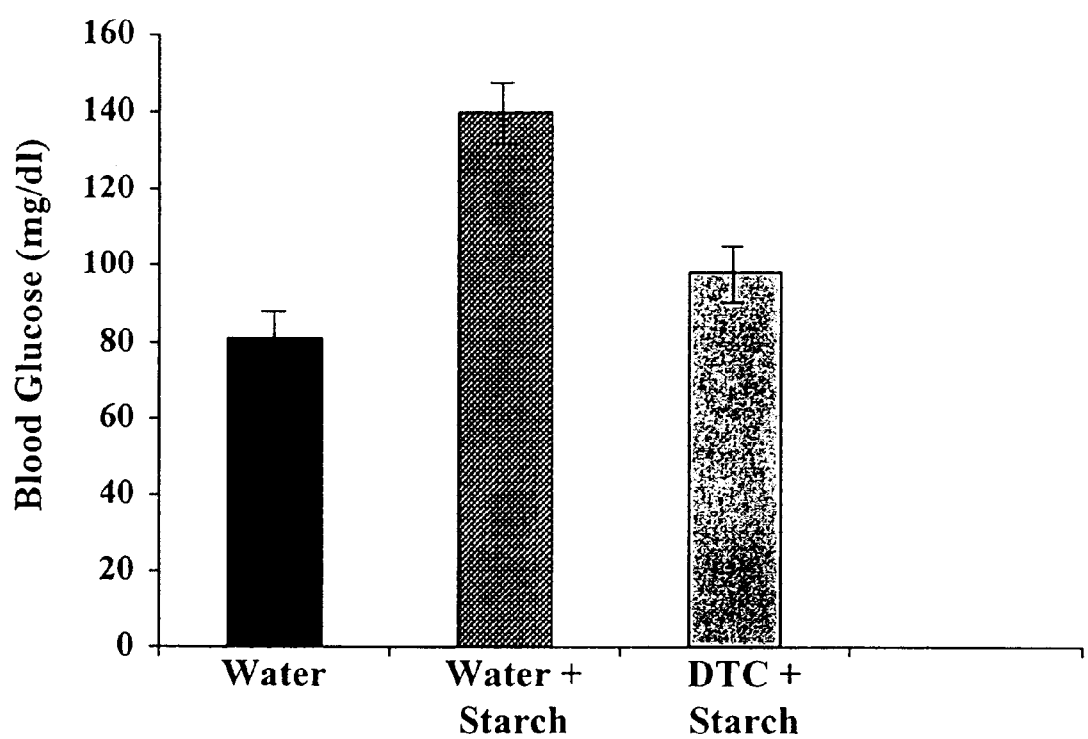
FIG. 3 shows the effect of MHCTD on the degradation of carbohydrates into monosaccharides. WF rats were treated with MHCTD or water for 2 weeks and fasted overnight. The rats were then intubated with hydrolyzed starch (2 g/kg) in water (2 g/20 ml) and blood glucose levels were determined 50 min after the intubation.

Carbohydrates in the diet must be degraded to monosaccharides by alpha-glucohydrolase in order to be absorbed in the gastrointestinal tract. In NIDDM patients there is less biologically active insulin to facilitate uptake of glucose. Therefore, the inhibition of complex carbohydrate degradation into monosaccharides may reduce the amount of absorbable glucose, resulting in a reduced requirement for insulin. To determine whether MHCTD treatment inhibits the degradation of complex carbohydrates into monosaccharides by the inhibition of alpha-glucohydrolase, we administered MHCTD and starch, water and starch, or water alone into WF rats and blood glucose levels were measured. We found that the blood glucose levels of WF rats that received MHCTD and starch were lower than that of WF rats administered water and starch but higher than that of WF rats administered water without starch (FIG. 3). As both insulin secretion and insulin action are normal in WF rats, these results suggest that the lower blood glucose levels in MHCTD-treated rats may result from a reduced degradation of complex carbohydrates.

Example 15

Effect of MHCTD on the Glucose Transporter

Figure 4:
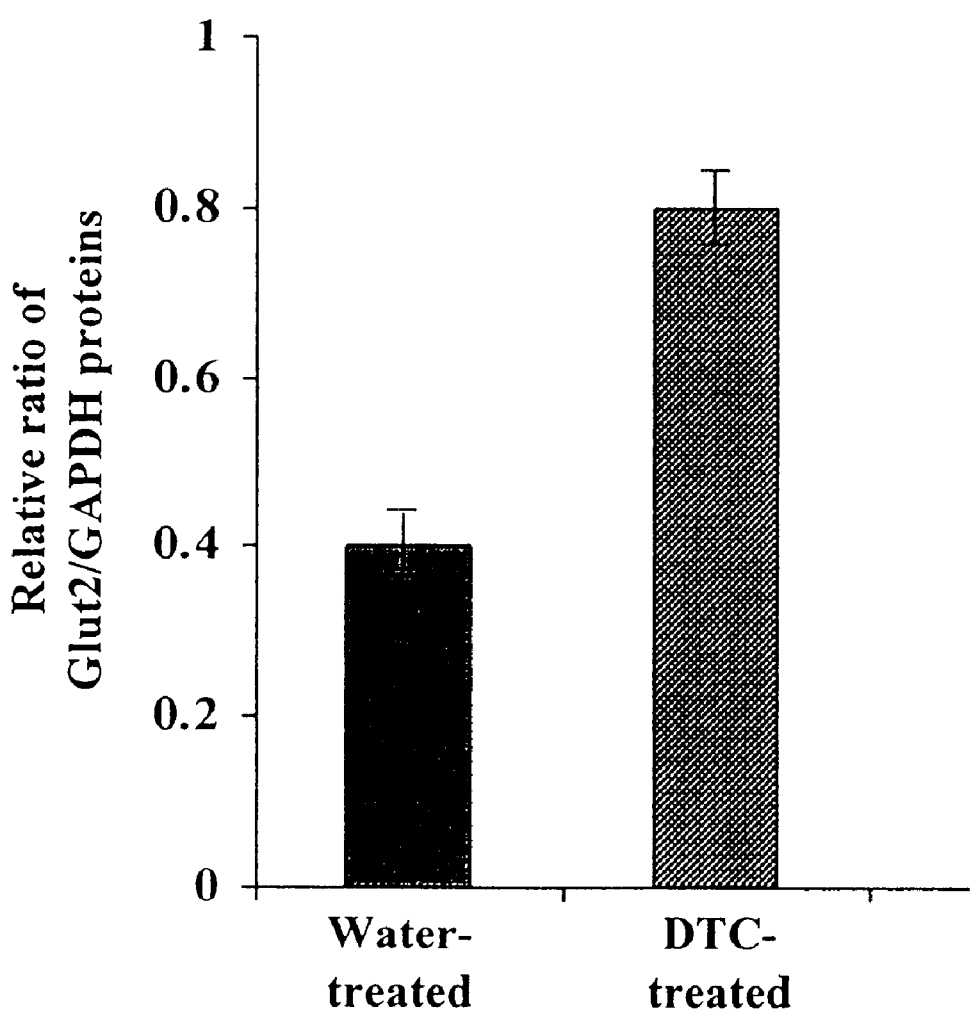
FIG. 4 shows the effect of MHCTD on the expression of glucose transporters. The pancreatic islets were isolated from GK rats that were treated with MHCTD or water. After the cell extracts were prepared, western blotting was performed with anti-Glut2 antibody and the expression level of Glut2 was analyzed by densitometry and normalized by the band intensity of GAPDH protein.

Glucose enters the beta cells through a membrane-bound facilitated transporter, Glut2. It has been suggested that impaired glucose entry into beta cells results in decreased glucose-induced insulin secretion in NIDDM patients. In animal models, it was reported that the expression of Glut2 protein is markedly decreased in the beta cells. Therefore, we determined the level of Glut2 protein in the pancreatic beta cell by western blotting, and found that the expression of Glut2 protein was significantly increased (about 2-fold) in the pancreatic beta cells of MHCTD-treated GK rats compared to water-treated GK rats (FIG. 4).

Example 16

Toxic Effect of MHCTD on Various Organs

Normal WF rats were administered MHCTD at a dose 10 times higher than the regular dose (50 g/kg body weight) daily for 5 months beginning at 3 months of age. At the end of the treatment, the animals were sacrificed and major organs including the stomach, testes, adrenal glands, thyroid gland, thymus, lung, heart, kidney, liver, brain and pancreas were removed. Sections of each organ were stained with hematoxylin and eosin and examined under the light microscope. Sections of stomach showed intact mucosa and no sign of inflammatory cell infiltration or other cellular injury. Lung sections showed normal appearing alveoli, bronchioles, bronchi and vessels. Heart sections showed normal endocardium and myocardium. Kidney sections showed intact glomeruli, tubules and vessels. There was no interstitial lymphocytic infiltration or necrosis. The lobules of the liver were well defined and the cords of hepatocytes were clearly separated by anastomosing sinuses and the central vein. There was no sign on lymphocytic infiltration, necrosis or intranuclear glycogen infiltration. Brain sections showed intact nerve and glial cells in the cerebral cortex. There was no evidence of necrosis, hemorrhage or infarction. Pancreatic sections showed an intact morphology of both the endocrine islet and exocrine acinar cells. There was no evidence of lymphocytic infiltration or necrosis. These results indicate that treatment with a high dose of MHCTD does not result in deleterious effects on the major organs examined (FIG. 5).

Example 17

Effect of MHCTD on the Control of Blood Glucose in NIDDM Patients

To determine whether MHCTD can control blood glucose in patients with NIDDM, randomly selected volunteers who had been diabetic for 3–7 years were treated with MHCTD. We found that all of these patients showed a significant decrease in blood glucose (Table 4). Three (YWB, KSW, OSW) of these 9 patients that had blood glucose levels close to 400 mg/dl (382–398 mg/dl) before treatment showed blood glucose levels around 140 mg/dl (114–162 mg/dl) after treatment. In addition, 4 other patients (LTW, JKS, YCS, PKH) who had blood glucose levels from 412–462 mg/dl before treatment showed blood glucose levels of around 160 mg/dl (121–184 mg/dl) after treatment. The two patients who had blood glucose levels from 476–510 mg/dl (SBS, CSS) before treatment showed blood glucose levels of around 200 mg/dl (194–214 mg/dl) after treatment. This result indicates that treatment of diabetic patients with MHCTD results in the significant decrease of blood glucose levels in all the patients tested.

To determine whether the termination of MHCTD treatment would reverse the level of blood glucose, we stopped MHCTD treatment of the patients for two months and then measured blood glucose levels. We found that there was no significant change in blood glucose in all the diabetic patients tested (Table 4).

We also tested 65 additional diabetic patients. These patients were divided into 4 groups on the basis of blood glucose levels before MHCTD treatment: group A—blood glucose levels between 200–300 mg/dl, group B—blood glucose levels between 301–400 mg/dl, group C—blood glucose levels between 401–500 mg/dl and group D—blood glucose levels between 501–600 mg/dl. In group A, about 65% ($^{15}/_{23}$) of the MHCTD-treated patients showed a reduction of blood glucose (below 150 mg/dl), about 13% ($^{3}/_{23}$) showed a reduction in their blood glucose level below 200 mg/dl, and there was no significant change (201–300 mg/dl) in the rest of the patients (22%; $^{5}/_{23}$). In group B, 43% ($^{12}/_{28}$) of the MHCTD-treated patients showed a decrease in blood glucose levels below 150 mg/dl, 32% ($^{9}/_{28}$) showed blood glucose levels between 151–200 mg/dl, 14% ($^{4}/_{28}$) showed blood glucose levels between 201–300 mg/dl, and 11% ($^{3}/_{28}$) showed no significant change in blood glucose levels (301–400 mg/dl). In group C, about 17% ($^{2}/_{12}$) of the MHCTD-treated patients showed a decrease in their blood glucose levels below 150 mg/dl, 67% ($^{8}/_{12}$) showed blood glucose levels between 151–200 mg/dl, and 17% ($^{2}/_{12}$) showed no significant change in blood glucose levels (250–500 mg/dl). In group D patients, one out of two patients treated with MHCTD showed a blood glucose level below 150 mg/dl, and the other showed a blood glucose level of 291 mg/dl (Table 5).

All of the references cited herein are incorporated by reference herein in their entirety.

Those skilled in the art will recognize, or be able to ascertain using no more than routine experimentation, many equivalents to the specific embodiments of the invention specifically described herein. Such equivalents are intended to be encompassed in the scope of the following claims.

TABLE 1

Effect of MHCTD on blood glucose level in GK rats[1]

| Treatment | Duration of treatment (months) | Mean blood glucose (mg/dl ± SD) | Incidence of diabetes (%) |
|---|---|---|---|
| MHCTD | 0 | 392 ± 28 | 90 (27/30) |
|  | 1 | 321 ± 29 | 77 (23/30) |
|  | 2 | 268 ± 35 | 60 (18/30) |
|  | 3 | 223 ± 38 | 40 (12/30) |
|  | 4 | 183 ± 39 | 27 (8/30) |
|  | 5 | 143 ± 43 | 13 (4/30) |
| Water | 0 | 381 ± 25 | 90 (27/30) |
|  | 1 | 386 ± 27 | 90 (27/30) |
|  | 2 | 392 ± 19 | 90 (27/30) |
|  | 3 | 395 ± 17 | 93 (28/30) |
|  | 4 | 389 ± 21 | 93 (28/30) |
|  | 5 | 393 ± 17 | 93 (28/30) |

[1]GK rats at 3 months of age were intubated with MHCTD or water. The mean non-fasting blood glucose levels of normal non-diabetic WF rats is 143 ± 19 mg/dl. Any GK rats that had a blood glucose level of 5 SD above this mean (over 238 mg/dl) were considered diabetic (n = 30/group).

TABLE 2

Effect of MHCTD on blood glucose levels in GK rats after termination of treatment.[1]

| Months after termination of treatment | Mean blood glucose (mg/dl ± SD) | Incidence of diabetes (%) |
|---|---|---|
| 0 | 143 ± 43 | 13 (4/30) |
| 1 | 152 ± 38 | 17 (5/30) |
| 2 | 160 ± 39 | 17 (5/30) |
| 3 | 171 ± 42 | 20 (6/30) |
| 4 | 174 ± 47 | 20 (6/30) |

[1]GK rats were treated with MHCTD for 5 months as described in Example 10. Blood glucose levels were monitored for 4 months after termination of the treatment.

TABLE 3

Effect of MHCTD on the prevention of NIDDM in GK rats.[1]

| Treatment | Age of animal (weeks) | Mean blood glucose (mg/dl ± SD+) | Incidence of diabetes (%) |
|---|---|---|---|
| MHCTD | 3 | 145 ± 29 | 0 (0/20) |
|  | 5 | 152 ± 31 | 0 (0/20) |
|  | 7 | 163 ± 35 | 5 (1/20) |
|  | 9 | 172 ± 42 | 10 (2/20) |
|  | 11 | 168 ± 39 | 10 (2/20) |
|  | 13 | 171 ± 40 | 10 (2/20) |
| Water | 3 | 147 ± 33 | 0 (0/20) |
|  | 5 | 172 ± 28 | 0 (0/20) |
|  | 7 | 218 ± 45 | 20 (4/20) |
|  | 9 | 320 ± 51 | 65 (13/20) |
|  | 11 | 368 ± 39 | 85 (17/20) |
|  | 13 | 376 ± 31 | 85 (17/20) |

[1]GK rats were treated with MHCTD or water from 3 weeks of age for 2 months, and blood glucose levels were determined weekly.

TABLE 4

Effect of MHCTD on the control of blood glucose in NIDDM patients.

| Patient | Duration of diabetes (years) | Blood glucose level before treatment (mg/dl) | Blood glucose level after 3 months of treatment (mg/dl) | Blood glucose level 2 months after termination of treatment (mg/dl) |
|---|---|---|---|---|
| YWB | 3 | 382 | 126 | 139 |
| KSW | 3 | 396 | 162 | 174 |
| OSW | 3 | 398 | 114 | 128 |
| LTW | 4 | 412 | 184 | 198 |
| JKS | 5 | 424 | 148 | 176 |
| YCS | 3 | 426 | 121 | 146 |
| PKH | 5 | 462 | 126 | 131 |
| SBS | 6 | 476 | 214 | 248 |
| CSS | 7 | 510 | 194 | 216 |

[1]NIDDM patients were treated with MHCTD as described in Example 17 for 3 months, and blood glucose levels were determined. Blood glucose levels were measured again 2 months after termination of the treatment. Patients who had been diabetic for 3 years did not receive any other medication at the time of treatment. Patients who had been diabetic for 4–5 years took sulfonylurea for 1 month after commencement of MHCTD treatment, and then terminated the treatment. Patients who had been diabetic 6–7 years took sulfonylurea for 2 months after commencement of MHCTD treatment, and then terminated the treatment.

TABLE 5

Effect of MHCTD on the control of blood glucose in 65 NIDDM patients.[1]

| Group | Before Treatment | | After treatment | |
|---|---|---|---|---|
|  | Blood glucose level (mg/dl) | Number of patients | Blood glucose level (mg/dl) | Number of patients |
| A | 200–300 | 23 | 101–150 | 15 |
|  |  |  | 151–200 | 3 |
|  |  |  | 201–250 | 3 |
|  |  |  | 252–300 | 2 |
| B | 301–400 | 28 | 101–150 | 12 |
|  |  |  | 151–200 | 9 |
|  |  |  | 201–250 | 1 |
|  |  |  | 251–300 | 3 |
|  |  |  | 301–350 | 1 |
|  |  |  | 351–400 | 2 |
| C | 401–500 | 12 | 101–150 | 2 |
|  |  |  | 151–200 | 8 |
|  |  |  | 250–500 | 2 |
| D | 501–600 | 2 | 101–150 | 1 |
|  |  |  | 251–300 | 1 |

[1]Sixty-five randomly selected NIDDM patients were treated with MHCTD for 3–6 months. Patients with blood glucose levels of 200–300 mg/dl did not receive any medication. Patients with blood glucose levels of 301–400 mg/dl, and took sulfonyl urea for only 1 month after commencement of MHCTD treatment. Patients with blood glucose levels of 401–500 mg/dl took sulfonylurea for only 2 months after commencement of MHCTD treatment. Patients with blood glucose levels of 501–600 mg/dl took sulfonylurea and received insulin injections for only 2 months after commencement of MHCTD treatment. Blood glucose levels were measured one hour after meals.

What is claimed is:

1. A hypoglycemic effective composition comprising extracts from *Pterocarpus marsupium, Morus alba, Orthosiphon aristatus, Opiophogon japonicus, Anemarrhena asphodeloides,* or *Trichosanthis kirilowii,* in combination with extracts from *Rosa rugosa* and/or *Commelina communis,* and a pharmaceutically acceptable carrier thereof, wherein said extracts are present in a ratio of:

about 20% by weight of *Pterocarpus marsupium,*
about 15% by weight of *Morus alba,*
about 20% by weight of *Orthosiphon aristatus,*
about 10% by weight of *Opiophogon japonicus,* about 8% by weight of *Rosa rugosa*,
about 7% by weight of *Commelina communis*,
about 10% by weight of *Trichosanthis kirilowii*, and
about 10% by weight of *Anemarrhena asphodeloides*.

2. The composition according to claim 1, wherein said carrier is a base of berries or fruit, a base of vegetable soup or bouillon, a soya-milk drink, or a nutritive supplement.

3. The composition according to claim 2, wherein said base of berries or fruit comprises extracts from *Rosa canina*, *Vaccinum myrtillus* or *Vaccinum vitis-idea*.

4. The composition according to claim 2, wherein said base of vegetable soup or bouillon comprises extracts from *Urtica diotica* leaves, *Allium cepa*, or *Ocimum sanctum*.

5. The composition according to claim 1, which further comprises extracts from *Arctium lappa* root, *Eugenia jambolana* seeds, *Phaseus vulgaris* husks, *Trigonella foenum graeam* seeds, or *Vaccinum myrtillus* leaves.

6. The composition according to claim 1, which further comprises chromium, manganese, zinc, niacin, vitamin B6 or vitamin B12.

7. The composition according to claim 6, wherein said chromium is present in an amount of about 20 to about 500 micrograms, manganese is present in an amount of about 1 to about 10 milligrams, zinc is present in an amount of about 2 to about 10 milligrams, niacin is present in an amount of about 50 to about 500 milligrams, vitamin B6 is present in an amount of about 1 to about 50 milligrams, or vitamin B12 is present in an amount of about 5 to about 100 micrograms per dose.

8. The composition according to claim 1, which further comprises extracts from Acanthopanax, Schizandra, and optionally Rhodiola.

9. The composition according to claim 5, which further comprises chromium, manganese, zinc, niacin, vitamin B6 or vitamin B12.

10. The composition according to claim 5, which further comprises extracts from Acanthopanax, Schizandra, and optionally Rhodiola.

11. The composition according to claim 6, which further comprises extracts from Acanthopanax, Schizandra, and optionally Rhodiola.

12. The composition according to claim 9, which further comprises extracts from Acanthopanax, Schizandra, and optionally Rhodiola.

13. The composition according to claim 8, wherein the extracts of *Acanthopanax senticosus* root, *Schizandra chinensis* fruit and seed, and *Rhodiola rosea* root are present in a ratio of about 4:2:1.

14. A method of treating type II diabetes comprising administering to a person in need thereof a hypoglycemic effective amount of the composition according to claim 1.

15. A method of reducing blood glucose level in a patient who has blood glucose level of about 200 to about 300 mg/dl at the beginning of treatment, comprising administering to said patient a hypoglycemic effective amount of the composition according to claim 1.

16. A method of increasing insulin secretion from pancreatic β cells, comprising administering an effective amount of the composition according to claim 1 to an individual.

17. A method of inhibiting degradation of complex carbohydrates to monosaccharides, comprising administering the composition according to claim 1 to an individual.

* * * * *